US006797127B1

United States Patent
Murata et al.

(10) Patent No.: US 6,797,127 B1
(45) Date of Patent: Sep. 28, 2004

(54) PROCESS AND APPARATUS FOR PURIFICATION OF OXYGEN-CONTAINING GAS

(75) Inventors: Toshiaki Murata, Tokyo (JP); Masamichi Kikuchi, Tokyo (JP); Kazuo Abe, Tokyo (JP)

(73) Assignee: Mitsui Engineering & Shipbuilding Co., Ltd and Eco-Logy Corporation, Tokyo (JP)

( * ) Notice: Subject to any disclaimer, the term of this patent is extended or adjusted under 35 U.S.C. 154(b) by 0 days.

(21) Appl. No.: 10/031,545

(22) PCT Filed: Jul. 11, 2000

(86) PCT No.: PCT/JP00/04625

§ 371 (c)(1),
(2), (4) Date: Apr. 4, 2002

(87) PCT Pub. No.: WO01/05441

PCT Pub. Date: Jan. 25, 2001

(30) Foreign Application Priority Data

Jul. 19, 1999 (JP) .......................................... 11/204763
Dec. 10, 1999 (JP) .......................................... 11/351940
Jan. 31, 2000 (JP) ...................................... 2000/022384

(51) Int. Cl.$^7$ ........................... C01B 13/00; A61L 2/00; B01J 19/12
(52) U.S. Cl. .................... 204/158.2; 422/24; 422/186.3
(58) Field of Search ........................ 204/158.2; 422/24, 422/186.3

(56) References Cited

U.S. PATENT DOCUMENTS 5,874,701 A  2/1999  Watanabe et al.
6,414,213 B2 * 7/2002 Ohmori et al. ............. 588/227

FOREIGN PATENT DOCUMENTS

| JP | 02280818 A | * | 11/1990 | ........... B01D/53/36 |
| JP | 0532039 U | * | 4/1993 | |
| JP | 10155887 A | * | 9/1998 | ........... A61L/9/015 |
| JP | 10249356 A | * | 9/1998 | ............. C02F/1/50 |
| WO | WO 9411092 A1 | * | 5/1994 | ........... B01D/53/36 |

OTHER PUBLICATIONS

References N–Q were cited on the International Search Report.*

* cited by examiner

*Primary Examiner*—Edna Wong
(74) *Attorney, Agent, or Firm*—Fay, Sharpe, Fagan, Minnich & McKee, LLP

(57) ABSTRACT

A method comprising a first step for radiating ultraviolet rays of a short wavelength of 110 nm or longer, but shorter than 200 nm to the gas, for example, an air to be treated to generate ozone, a second step for radiating ultraviolet rays of a medium wavelength of 200 nm or longer, but shorter than 300 nm to the air treated in the first step to form active oxygen, and a third step for radiating ultraviolet rays of a long wavelength of 300 nm or longer, but shorter than 380 nm to the air treated in the second step to convert the active oxygen into oxygen molecule in ground state, at least the second and/or third step being conducted in the presence of a photocatalyst comprising particles of titanium oxide of an orthorhombic crystal system or particles of titanium oxide of an orthorhombic crystal system supporting fine particles of another metal.

7 Claims, 1 Drawing Sheet

PROCESS AND APPARATUS FOR PURIFICATION OF OXYGEN-CONTAINING GAS

TECHNICAL FIELD

The present invention relates to a method and an apparatus for purifying an oxygen containing gas. More specifically, the present invention relates to a method and an apparatus for purifying an oxygen containing gas by which not only an air can be disinfected or deodorized and an air which is preferably used for clean rooms can be purified, but also hardly decomposable organic compounds contained in an air and inorganic air pollutants such as NOx, SOx, CO, and ammonia can be decomposed to make them harmless.

BACKGROUND ART

As methods for purifying an oxygen containing gas (hereinafter, sometimes referred to as an air for brevity), (1) a method wherein ozone is generated in an air by using an ozone generating device and then diffused, (2) a method wherein disinfection of an air is performed by using a germicidal lamp, and (3) a method wherein an HEPA (high efficiency particulate air) filter or a chemical filter which is installed for clean rooms or others is used are heretofore known.

However, there are such problems that the ozone diffusing method of (1) emits ozone which is harmful to human bodies; that the method of (2) can not instantaneously disinfect a large quantity of air since the method principally uses ultraviolet rays of a wavelength of 254 nm and thus does not form active oxygen, and the method of (2) does not have an effect in the shadow portions of an germicidal lamp; and further that the method of (3) using an HEPA filter only captures bacteria with the filter, does not have an effect of disinfection, and has defects such that when a chemical filter is used, a long time is required for exchanging the filter whereas a disinfecting effect can be produced, and when a time appropriate for exchanging the filter was past, bacteria propagate contrary to expectations. Besides, it was impossible by the methods described above to decompose and remove hardly decomposable organic compounds, for example, chlorine containing aromatic compounds when these compounds are contained in an air to be treated.

DISCLOSURE OF THE INVENTION

An object of the present invention is to resolve the problems in conventional technology described above and to provide a method and an apparatus for purifying an air by which a large quantity of an air to be treated (hereinafter, sometimes the words "to be treated" are omitted for brevity) can instantaneously be disinfected, deodorized, and purified, and an air which is harmless to men and beasts can be regenerated. Another object of the present invention is to provide a method and an apparatus for purifying an air by which chains between carbon atoms, for example, single bonds, double bonds, triple bonds in hardly decomposable organic compounds can be severed to decompose the compounds into low molecular weight compounds such as carbonic acid gas and water even when the hardly decomposable organic compounds are contained in an air.

The method for purifying an air according to the present invention is characterized by radiating ultraviolet rays to an air in the presence of a photocatalyst comprising titanium oxide. More specifically, the method of the present invention for purifying an air comprises a first step for radiating ultraviolet rays of a short wavelength of, for example, 110 nm or longer, but shorter than 200 nm to an air to generate ozone in the air, a second step for further radiating ultraviolet rays of a medium wavelength of 200 nm or longer, but shorter than 300 nm to the air treated in the first step to form active oxygen, and a third step for still further radiating ultraviolet rays of a long wavelength of 300 nm or longer, but shorter than 380 nm to the air treated in the second step to convert the active oxygen into oxygen molecule in ground state, at least the second and/or the third step being conducted in the presence of a photocatalyst. The step for generating ozone in an air is not limited to a step wherein the ultraviolet rays described above are radiated, but includes a step wherein silent discharge is conducted in an air.

The photocatalyst generally comprises particles of a photo-semiconductor such as titanium dioxide. When desired, the photocatalyst comprises particles in which fine particles of a metal such as silver are supported as an electrode on the particles of the photo-semiconductor. As the particles of a photo-semiconductor, particles of titanium oxide of a tetragonal crystal system (anatase type or rutile type) well known in the art can be used, but particles of titanium oxide of an orthorhombic crystal system or particles of titanium oxide of an orthorhombic crystal system supporting fine particles of another metal are desirably used in particular. As the particles of titanium oxide of an orthorhombic crystal system, particles of brookite are most desirable. Particles of titanium oxide of a different crystal system or particles of a photo-semiconductor other than titanium oxide may be used together.

In the method of the present invention, the air treated in the third step described above is preferably dried by further irradiating the air with rays (usually or mainly infrared rays) radiated from an infrared lamp and with rays (mainly near infrared rays) radiated from a halogen lamp. In this connection, while the method of the present invention can be applied for purifying various gases containing oxygen, the method is most advantageously applied for purifying an air.

The apparatus of the present invention for purifying an air comprises a first treating room having means for supplying the air and a device for generating ozone in the air, for example, a device for radiating ultraviolet rays of a short wavelength of 110 nm or longer, but shorter than 200 nm to the air, a second treating room connected to the first treating room and having a device for radiating ultraviolet rays of a medium wavelength of 200 nm or longer, but shorter than 300 nm to the air supplied from the first treating room, a third treating room connected to the second treating room and having a device for radiating ultraviolet rays of a long wavelength of 300 nm or longer, but shorter than 380 nm to the air supplied from the second treating room, and means for discharging the air treated in the third treating room outside the apparatus, the second and/or the third treating room having a photocatalyst.

As the photocatalyst used in the apparatus, the same as or similar to the apparatus described above with respect to the method of the present invention can be used.

The apparatus of the present invention is preferably provided, in the third treating room described above, with a drying room wherein a portion for irradiating an oxygen containing gas with rays radiated from an infrared lamp and a portion for irradiating the oxygen containing gas with rays radiated from a halogen lamp are installed.

While the apparatus of the present invention can also be applied for purifying various gases containing oxygen, the apparatus is most advantageously applied for purifying an air.

Figure 1:
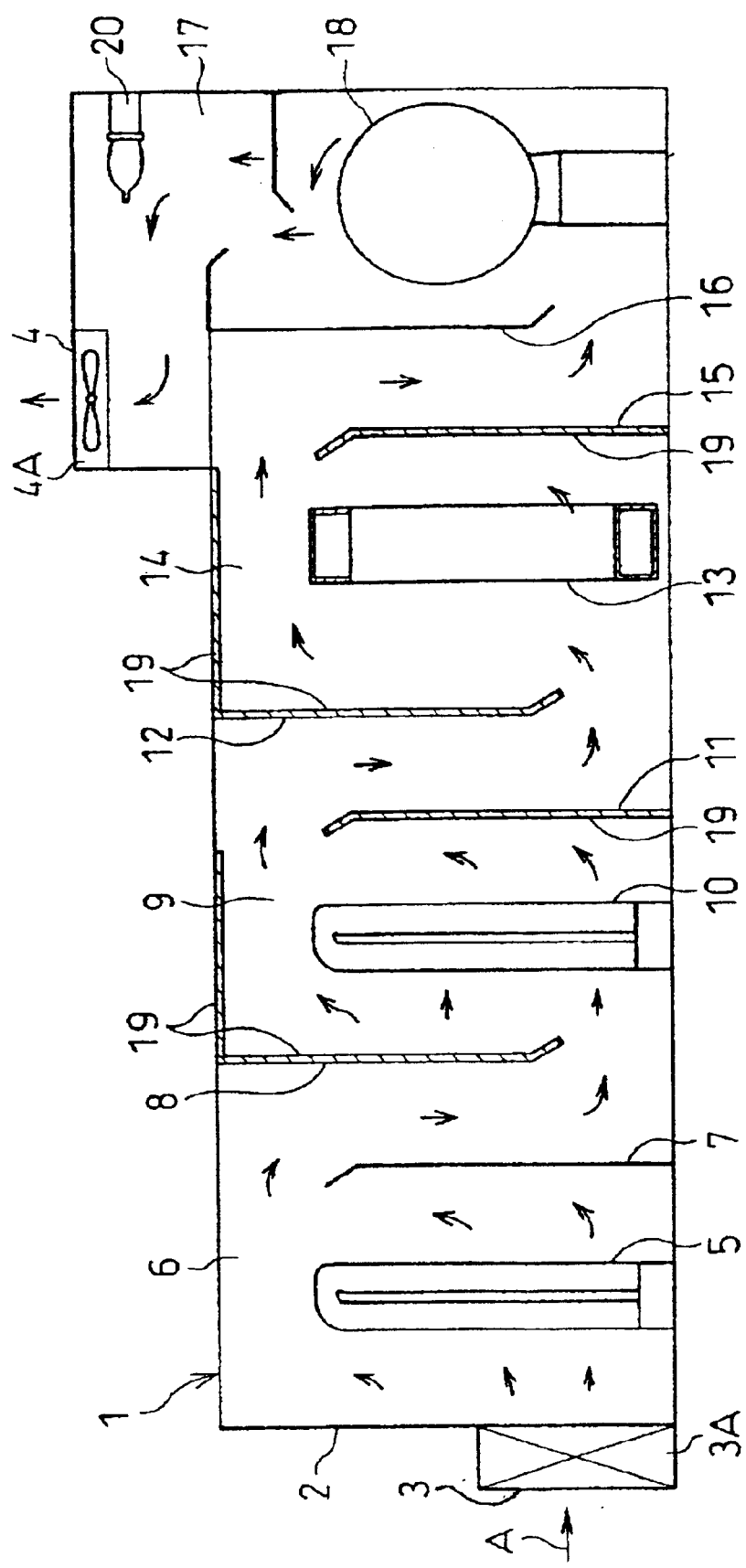
FIG. 1 is a schematic drawing for illustrating an example of the apparatuses of the present invention for purifying an air.

The symbols shown in the drawing indicate the following devices, parts, portions, and the like, respectively. 1 . . . an apparatus for purifying an air, 2 . . . a casing, 3 . . . an air introducing port, 3A . . . a filter, 4 . . . an air discharging port, 4A . . . a suction blower, 5 . . . a device for radiating ultraviolet rays of a short wavelength, 6 . . . a first treating room, 7, 8, 11, 12, 15, and 16 . . . partition walls, 9 . . . a second treating room, 10 . . . a device for radiating ultraviolet rays of a medium wavelength, 13 . . . a device for radiating ultraviolet rays of a long wavelength, 14 . . . a third treating room, 17 . . . a drying room, 18 . . . an infrared lamp, 19 . . . a photocatalyst, 20 . . . a halogen lamp, A . . . an air.

BEST EMBODIMENT FOR CARRYING OUT THE INVENTION

The present invention is to form oxygen in singlet state and super oxide which are sources of active oxygen by radiating ultraviolet rays to an air, particularly to promote the generation of the sources of active oxygen described above by conducting irradiation with ultraviolet rays of a medium wavelength and with ultraviolet rays of a long wavelength in the presence of a specific photocatalyst at that time, and not only to disinfect and deodorize the air but also to decompose hardly decomposable organic compounds contained in the air by a large energy (a little over 22.5 kcal/mol) of the active oxygen sources.

The behavior (in a dried atmosphere) of oxygen caused by irradiation with ultraviolet rays of each of the wavelengths preferably used in the present invention is shown below.

(1) Irradiation with ultraviolet rays of a short wavelength (110 to 200 nm):

$O_2 + h\nu$ (ultraviolet rays of a short wavelength in a vacuum ultraviolet region) $\rightarrow 2O$ ($^3P$) (oxygen atom in ground state)

$O(^3P) + O_2 \rightarrow O_3$ (ozone)

(2) Irradiation with ultraviolet rays of a medium wavelength (200 to 300 nm):

$O_3 + h\nu$ (ultraviolet rays of a medium wavelength which is a DNA absorption wavelength) $\rightarrow 2O$ ($^1D$) (oxygen atom in singlet state) $+ O_2$ ($^1\Delta$) (oxygen molecule in singlet state)

$2O$ ($^1D$) $\rightarrow O_2$ (super oxide)

In a humid atmosphere, the following reaction also occurs:

$O(^1D)$ (oxygen atom in singlet state) $+ H_2O \rightarrow 2 \cdot OH$ (hydroxy radical)

(3) Irradiation with ultraviolet rays of a long wavelength (300 to 380 nm):

$2O$ ($^1D$) $+ h\nu$ (ultraviolet rays of a long wavelength) $\rightarrow$
$O_2$ (oxygen molecule in ground state)

$O_2^-$ (super oxide) $+ h\nu$ (ultraviolet rays of a long wavelength) $\rightarrow O_2$ (oxygen molecule in ground state)

In a humid atmosphere, the following reaction also occurs:

$2 \cdot OH$ (hydroxy radical) $\rightarrow O(^3P)$ (oxygen atom in ground state) $+ H_2O$ In the irradiation with ultraviolet rays of a medium wavelength and the irradiation with ultraviolet rays of a long wavelength, when a photocatalyst is present, electrons are ejected on the surface of a catalyst, the electrons act on oxygen atoms in ground state to form active oxygen anions, and the active oxygen anions bond each other to form super oxides having a strong disinfecting power. Further, the super oxides are converted into oxygen atoms in ground state by receiving radiation of ultraviolet rays of a long wavelength.

$h\nu$ (ultraviolet rays of a medium wavelength of 200 to 300 nm) $\rightarrow$ Hole$^+$ (positive hole on a catalyst) $+ e^-$ (electron ejected on the surface of the catalyst)

$e^- + (^3P)$ (oxygen atom in ground state) $\rightarrow O^-$ (active oxygen anion)

$2O^-$ (active oxygen anion) $\rightarrow O_2^-$ (super oxide)

$O_2^-$ (super oxide) $+ h\nu$ (ultraviolet rays of a long wavelength of 300 to 370 nm) $\rightarrow O_2$ (oxygen molecule in ground state)

In a humid atmosphere, the following reaction also occurs:

Hole$^+ + OH^- \rightarrow \cdot OH$ (hydroxy radical)

In the method and the apparatus of the present invention, all oxygen containing gases such as exhaust gases containing hardly decomposable organic compounds or inorganic air pollutants, in addition to an air which contains bacteria or odor, are the objects of the purification.

The photocatalyst used in the present invention comprises particles of titanium oxide as particles of a photo-semiconductor or particles of the titanium oxide supporting, as an electrode, fine particles of a metal such as silver. The photocatalyst is coated with an adsorption material such as powders of a ceramic, when necessary. As the titanium oxide, while an anatase type or rutile type titanium oxide of a tetragonal crystal system, and titanium oxide of orthorhombic crystal system can be used, titanium oxide of an orthorhombic crystal system is preferably used in the present invention. As the particles of titanium oxide of an orthorhombic crystal system, particles of brookite are specifically mentioned, and the brookite may be a natural product or synthesized product. The titanium oxide (TiO$_2$) particles may comprise particles of a different crystal system as a component of the particles when necessary, and can be used in a mixture with particles of another photo-semiconductor, for example, CdS, CdSe, WO$_3$, Fe$_2$O$_3$, SrTiO$_3$, or KNbO$_3$. As fine particles of a metal used as an electrode, fine particles of gold, platinum, or copper can be used in addition to silver particles. The diameter of the particles of a photo-semiconductor is preferably in the range of 1 to 50 $\mu$m. The diameter of fine particles of a metal is preferably 0.05 to 0.1 $\mu$m. The mixing ratio of particles of a photo-semiconductor with fine particles of a metal is preferably 1 to 55 parts by weight and desirably 20 to 30 parts by weight in particular of the metal fine particles per 100 parts by weight of the photo-semiconductor particles to suitably exert their disinfecting and deodorizing actions. The adsorption material is used to adsorb bacteria and viruses from an air and maintain them, and an activated carbon and silk fiber containing product in addition to powders of a ceramic, for example, powders of apatite (asparagus stone), zeolite, or sepiolite can be used. As the apatite, hydroxy apatite [Ca$_{10}$(PO$_4$)$_6$(OH)$_2$] which selectively adsorbs bacteria and viruses is preferable. The particle diameter of these adsorption materials (in the case of a silk fiber containing product, the particle diameter of powders) is preferably 0.001 to 1.0 $\mu$m and desirably 0.01 to 0.05 $\mu$m in particular when securing a large surface area and a good adsorbing property are taken into consideration. The mixing ratio of particles of a photo-semiconductor with an adsorption material is preferably 1 to 50 parts by weight and desirably 10 to 30 parts by weight in particular of the adsorption material per 100 parts by weight of the photo-semiconductor particles.

In the present invention, a photocatalyst is adhered on a substrate to which an air contacts. As such substrate, a metallic plate, ceramic board, nonwoven fabric, for example, polyester fiber nonwoven fabric, paper, woven fabric, and plastic plate or sheet are mentioned. As the method for adhering the photocatalyst, a method wherein a photocatalyst is directly adhered to a substrate by a low temperature flame spray coating process without using a binder, and a sol-gel process, that is, a process wherein a sol comprising a photocatalyst (photo-semiconductor particles, metal fine particles, and an adsorbing material), a film forming component as inorganic binder, and a solvent is adhered on a substrate and then the sol is gelatinized, for example, at 300 to 400° C. are mentioned. In this case, other components may additionally be contained, when necessary.

In the low temperature flame spray coating process, for example, particles (5 to 50 $\mu$m) of titanium oxide having a melting point of lower than 2000° C. and fine particles (1 to 10 $\mu$m) of the metal described above are sprayed onto the substrate described above by a gas flame spray coating process using oxygen, acetylene, or the like, together with a ceramic melted at about 2900 to 3000° C. After the flame spray coating, the photocatalyst particles become particles in a flat and piled shape of 30 to 40 $\mu$m, and are strongly adhered on the substrate by an anchor effect by melting.

On the other hand, in the method wherein a binder is used, a resin used for forming a film such as a cellulose derivative, phthalic resin, phenol resin, and alkyd resin known in the public, talc, calcium carbonate, barium sulfate, barium carbonate, or glass in a shape of beads is used as film forming component. As the solvent, water, an alcohol type solvent such as ethanol and propanol, petroleum type solvent, and aromatic type solvent can be used. The total blending amount of particles of a photo-semiconductor, fine particles of a metal, and an adsorption material when they are coated as paint is preferably 3 to 55% by weight and desirably 15 to 35% by weight in particular based on the total amount of paint in order to exert actions such as disinfection and deodorization and to secure an appropriate coatability.

When a titanium oxide of tetragonal crystal system is used as photocatalyst, a titanium oxide in which all crystals are in a shape of anatase crystal has a strong oxidizing power and thus sometimes deteriorates the substrate. Accordingly, in such a case, it is preferable to make the weight ratio of anatase type crystals to rutile type crystals in titanium oxide powders, which are raw materials in the paint, 20 to 50%:50 to 80%. When the ratio of anatase type crystals is lowered, the action of the photocatalyst becomes weak that much.

On the other hand, when titanium oxide of an orthorhombic crystal system is used as catalyst, it is possible to sever chains between carbon atoms in organic compounds which were difficult to decompose by titanium oxide of anatase type or rutile type, and to decompose aromatic rings to convert the organic compounds back into simple compounds such as carbonic acid gas, water, and the like. However, since the action of the photocatalyst is strongest and the catalyst readily deteriorates substrate, it is necessary to use a substrate, paint, or the like which is hardly oxidized.

As fine particles of another metal, while powders of a metal such as vanadium and tungsten in addition to silver, gold, platinum, and copper having a good conductivity are used, powders of platinum are most preferable in the aspect that they are not changed with the passage of time and are stable. However, when cost efficiency is considered, powders of silver are preferable since they are nontoxic and have disinfecting property by themselves. Besides, from the aspect of producing a promoter effect, powders of vanadium or tungsten are preferable. The diameter of fine particles of these metals is preferably 0.001 to 0.1 $\mu$m when the relation with titanium oxide particles is considered. The mixing ratio of the titanium oxide particles described above with metal fine particles described above is preferably 1 to 55 parts by weight and more desirably 20 to 30 parts by weight of the metal fine particles per 100 parts by weight of the titanium oxide particles in order to suitably exert purifying action.

The radiation of ultraviolet rays is performed by using ultraviolet lamps which generate ultraviolet rays of the predetermined wavelengths described above and are available on the market, or performed by radiating ultraviolet rays through a silica glass which selectively transmits ultraviolet rays of a specific wavelength.

As devices for radiating ultraviolet rays used in the present invention, mercury lamps, metal halide lamps, ultraviolet lamps, and lamps for exciting a photocatalyst each generating ultraviolet rays of a predetermined wavelength can be used. As an ultraviolet lamp for radiating ultraviolet rays of a short wavelength, a chemical lamp can be used. Besides, as for ultraviolet rays of a short, medium, or long wavelength, ultraviolet mercury lamps can be used. The ultraviolet mercury lamps employ emission spectrum of mercury enclosed in a silica glass tube, are divided into a low pressure type (by which strong UV rays are produced in the range of wavelengths shorter than 245 nm) and a high pressure type (by which strong UV rays are produced in the range of wavelengths longer than 365 nm) by the pressure of mercury vapor in a lighted condition, and can be used for medium wavelengths and long wavelengths, respectively. Further, the lamps for exciting a photocatalyst include W type and N type fluorescent lamps having a peak at 351 nm and 368 nm, respectively (as described, for example, in Construction Equipments (Kenchlku Setsubi) and Pipe Arrangement (Haikan Kouji) No. 6, 1998, pages 47 to 50), and the W type and N type fluorescent lamps can be used for ultraviolet rays of a medium wavelength and a long wavelength, respectively. With respect to a photocatalyst, it is sufficient that the photocatalyst is adhered on the inside walls or partition walls in a room in which ultraviolet rays are radiated and through which an air is passed, and it is possible to install fin-like catalyst plates on the walls described above so that the catalyst plates cross the path of the air to increase a catalyst effect. As the devices for radiating the three kind of ultraviolet rays described above, a device generating at least ultraviolet rays of a wavelength of 183 to 184 nm, as a device for radiating ultraviolet rays of a short wavelength; a device generating at least ultraviolet rays of a wavelength of 254 nm, as a device for radiating ultraviolet rays of a medium wavelength; and a device generating at least ultraviolet rays of 310 to 370 nm, as a device for radiating ultraviolet rays of a long wavelength, are preferable.

Now, the present invention is described in more detail with reference to drawing.

FIG. 1 is a schematic drawing for illustrating an example of the apparatuses of the present invention for purifying an air. This apparatus 1 is mainly composed of casing 2 through which air A to be treated is passed, air introducing port 3 provided at an end of the casing 2 and having filter 3A, air discharging port 4 provided at the other end of the casing 2 and having suction blower 4A, three treating rooms of first treating room 6 having device 5 for radiating ultraviolet rays of a short wavelength, second treating room 9 connected to the first treating room 6 through partition walls 7 and 8 and having device 10 for radiating ultraviolet rays of a medium wavelength, and third treating room 14 connected to the second treating room 9 through partition walls 11 and 12 and having device 13 for radiating ultraviolet rays of a long wavelength provided in the direction from the air introducing port 3 toward the air discharging port 4 in order, and drying room 17 connected to the third treating room 14 through partition walls 15 and 16. Device 5 for radiating ultraviolet rays of a short wavelength generates ultraviolet rays of a wavelength of 110 nm or longer, but shorter than 200 nm (preferably 110 to 185 nm), device 10 for radiating ultraviolet rays of a medium wavelength generates ultraviolet rays of a medium wavelength of 200 nm or longer, but shorter than 300 nm (preferably 210 to 260 nm), and device 13 for radiating ultraviolet rays of a long wavelength generates ultraviolet rays of 300 nm or longer, but shorter than 380 nm (preferably 310 to 370 nm). Besides, on the partition walls 8 and 11 and the inside walls of the casing in the second treating room 9, and the partition walls 12 and 15 and the inside walls of the casing in the third treating room 14, photocatalyst 19 is adhered or coated.

Further, infrared lamp 18 is installed in drying room 17, and the drying room is arranged so that the air purified in the third treating room is discharged from air discharging port 4 after the air was dried. In each of the devices 5 and 10 for radiating ultraviolet rays, for instance, two electrodes are installed within a silica glass tube and vapor of a metal such as mercury under a predetermined pressure is enclosed in the tube so that ultraviolet rays of the specific wavelength described above are obtained by applying a predetermined potential difference to the electrodes. As device 13 for radiating ultraviolet rays of a long wavelength, the device forming ultraviolet rays of the long wavelength described above can be used.

In the apparatus described above, air A to be treated is introduced into first treating room 6 from air introducing port 3 after the air passed through filter device 3A, and subjected here to the irradiation with ultraviolet rays from device 5 for radiating ultraviolet rays of a short wavelength to generate ozone as described above. The bacteria and the like contained in the air is disinfected by the oxidizing action of the ozone. The air discharged from first treating room 6 is entered into second treating room 9 and then subjected here to the irradiation with ultraviolet rays from device 10 for radiating ultraviolet rays of a medium wavelength to form active oxygen such as oxygen molecules in singlet state and super oxides as described above by the action of the ultraviolet rays and the action of photocatalyst 19, thereby performing disinfection and deodorization of the air as well as oxidative destruction of the organic compounds. Then, the air containing such active oxygen is moved into third treating room 14, subjected here to the irradiation with ultraviolet rays from device 13 for radiating a long wavelength to convert the super oxides into oxygen molecules in ground state and further to purify the air by the energy released at that time. The purified air is moved into drying room 17, is dried by irradiation with infrared rays (heat rays) from infrared lamp 18, absorbs heat rays from halogen lamp 20, and then discharged outside from air discharging port 4.

The method and the apparatus of the present invention can widely be applied for treatments to make exhaust gases containing hardly decomposable organic compounds, for example, chlorine containing aromatic compounds such as dioxin or inorganic compounds such as NOx, SOx, CO, NH$_3$, and the like nontoxic, in addition to treatments for preventing nosocomial infection (infection by methicillin-resistant *Staphylococcus aureus* (MRSA) and the like), providing clean rooms used in medical care or food processing, or deodorizing the air within ducts or tobaccos.

EXAMPLE 1

By using a testing apparatus similar to that shown in FIG. 1, five kind in total of aerosols A containing bacteria ($10^8$ CFU/ml) or viruses ($10^7$ PFU/ml) were separately blown from air introducing port 3 of the testing apparatus into the apparatus. On the other hand, a filter for capturing organisms was fitted to air discharging port 4 and the organisms were trapped. From the filter, bacteria or viruses were emigrated, cultivated on the following mediums, and then determined. (Test was conducted twice.)

Bacteria and mediums, and viruses and cells:

*Escherichia coli* ATCC 35150 (pathogenic *escherichia coli* O-157)

Dezoxycolate medium

*Staphylococcus aureus* IFO 12732 (*staphylococcus aureus* MRSA)

Mannitol salt medium

*Pseudomonas aeruginosa* GNB-139 (*pseudomonas aeruginosa*)

NAC agar medium

*Bacillus subtilus* spore (*bachillus subtilus* spore)

Mannitol salt medium

*Coxsackie virus* Type B6 Schmitt strain

HEL-R66 cell (cell derived from human embryonic lung)

The number of survived bacteria or viruses, survival ratio, and disinfected ratio at the time when germicidal lamps in the testing apparatus were lighted up were determined with those at the time when the germicidal lamps were put out (only a fan (suction blower) was operated) being control. The combination of test conditions were six kinds of F (control), S, S+M, S+M+L, S+M+L+R, and S+M+L+R+H. Herein, F indicates that only the fan was operated (and all lamps were put out); S indicates that the fan was operated and device 5 for radiating ultraviolet rays of a short wavelength (S) was lighted up; M indicates that device 10 for radiating ultraviolet rays of a medium wavelength (M) was lighted up, L indicates that device 13 for radiating ultraviolet rays of a long wavelength (L) was lighted up; R indicates that infrared lamp 18 for radiating infrared rays (R) was lighted up; and H indicates that halogen lamp 20 (H) was lighted up, respectively. The results thus obtained are shown in Tables 1 to 5.

TABLE 1

Disinfecting effect on pathogenic *escherichia coli* 0–157 by an air disinfecting apparatus

| Germicidal lamp | Test | Number of survived bacteria CFU/filter | Survival ratio % | Disinfected ratio % |
|---|---|---|---|---|
| F (control) | 1 | $1.2 \times 10^3$ | 100 | 0 |
|  | 2 | $1.2 \times 10^3$ | 100 | 0 |
|  | Average | $1.2 \times 10^3$ | 100 | 0 |
| S | 1 | 20 | 1.7 | 98.3 |
|  | 2 | 10 | 0.8 | 99.2 |
|  | Average | 15 | 1.3 | 98.7 |
| S + M | 1 | <10 Not detected | <0.8 | >99.2 |
|  | 2 | <10 Not detected | <0.8 | >99.2 |
|  | Average | <10 Not detected | <0.8 | >99.2 |

TABLE 1-continued

Disinfecting effect on pathogenic
*escherichia coli* 0–157 by an
air disinfecting apparatus

| Germicidal lamp | Test | Number of survived bacteria CFU/filter | Survival ratio % | Dis-infected ratio % |
|---|---|---|---|---|
| S + M + L | 1 | <10 Not detected | <0.8 | >99.2 |
| | 2 | <10 Not detected | <0.8 | >99.2 |
| | Average | <10 Not detected | <0.8 | >99.2 |
| S + M + L + R | 1 | <10 Not detected | <0.8 | >99.2 |
| | 2 | <10 Not detected | <0.8 | >99.2 |
| | Average | <10 Not detected | <0.8 | >99.2 |
| S + M + L + R + H | 1 | <10 Not detected | <0.8 | >99.2 |
| | 1 | <10 Not detected | <0.8 | >99.2 |
| | Average | <10 Not detected | <0.8 | >99.2 |

F: Only the fan was operated (all lights were put out), S: the fan was operated and S was lighted up, M: M was lighted up, L: L was lighted up, R: R was lighted up, and H: H was lighted up.

TABLE 2

Disinfecting effect on *staphylococcus aureus*
MRSA by an air disinfecting apparatus

| Germicidal lamp | Test | Number of survived bacteria CFU/filter | Survival ratio % | Dis-infected ratio % |
|---|---|---|---|---|
| F (control) | 1 | 2.2 × 10³ | 100 | 0 |
| | 2 | 2.1 × 10³ | 100 | 0 |
| | Average | 2.2 × 10³ | 100 | 0 |
| S | 1 | 20 | 0.9 | 99.1 |
| | 2 | 10 | 0.5 | 99.5 |
| | Average | 15 | 0.7 | 99.3 |
| S + M | 1 | 20 | 0.9 | 99.1 |
| | 2 | 10 | 0.5 | 99.5 |
| | Average | 15 | 0.7 | 99.3 |
| S + M + L | 1 | <10 Not detected | <0.5 | >99.5 |
| | 2 | <10 Not detected | <0.5 | >99.5 |
| | Average | <10 Not detected | <0.5 | >99.5 |
| S + M + L + R | 1 | <10 Not detected | <0.5 | >99.5 |
| | 2 | <10 Not detected | <0.5 | >99.5 |
| | Average | <10 Not detected | <0.5 | >99.5 |
| S + M + L + R + H | 1 | <10 Not detected | <0.5 | >99.5 |
| | 2 | <10 Not detected | <0.5 | >99.5 |
| | Average | <10 Not detected | <0.5 | >99.5 |

F: Only the fan was operated (all lights were put out), S: the fan was operated and S was lighted up, M: M was lighted up, L: L was lighted up, R: R was lighted up, and H: H was lighted up.

TABLE 3

Disinfecting effect on *pseudomonas aeruginosa*
by an air disinfecting apparatus

| Germicidal lamp | Test | Number of survived bacteria CFU/filter | Survival ratio % | Dis-infected ratio % |
|---|---|---|---|---|
| F (control) | 1 | 1.2 × 10³ | 100 | 0 |
| | 2 | 1.1 × 10³ | 100 | 0 |
| | Average | 1.2 × 10³ | 100 | 0 |
| S | 1 | 30 | 2.5 | 97.5 |
| | 2 | 20 | 1.8 | 98.2 |
| | Average | 25 | 2.1 | 97.9 |

TABLE 3-continued

Disinfecting effect on *pseudomonas aeruginosa*
by an air disinfecting apparatus

| Germicidal lamp | Test | Number of survived bacteria CFU/filter | Survival ratio % | Dis-infected ratio % |
|---|---|---|---|---|
| S + M | 1 | <10 Not detected | <0.8 | >99.2 |
| | 2 | <10 Not detected | <0.9 | >99.1 |
| | Average | <10 Not detected | <0.8 | >99.2 |
| S + M + L | 1 | <10 Not detected | <0.8 | >99.2 |
| | 2 | <10 Not detected | <0.9 | >99.1 |
| | Average | <10 Not detected | <0.8 | >99.2 |
| S + M + L + R | 1 | <10 Not detected | <0.8 | >99.2 |
| | 2 | <10 Not detected | <0.9 | >99.1 |
| | Average | <10 Not detected | <0.8 | >99.2 |
| S + M + L + R + H | 1 | <10 Not detected | <0.8 | >99.2 |
| | 2 | <10 Not detected | <0.9 | >99.1 |
| | Average | <10 Not detected | <0.8 | >99.2 |

F: Only the fan was operated (all lights were put out), S: the fan was operated and S was lighted up, M: M was lighted up, L: L was lighted up, R: R was lighted up, and H: H was lighted up.

TABLE 4

Disinfecting effect on *bacillus subtilus* spore
by an air disinfecting apparatus

| Germicidal lamp | Test | Number of survived bacteria CFU/filter | Survival ratio % | Dis-infected ratio % |
|---|---|---|---|---|
| F (control) | 1 | 1.5 × 10³ | 100 | 0 |
| | 2 | 1.4 × 10³ | 100 | 0 |
| | Average | 1.5 × 10³ | 100 | 0 |
| S | 1 | 30 | 2.0 | 98.0 |
| | 2 | 20 | 1.4 | 98.6 |
| | Average | 25 | 1.7 | 98.3 |
| S + M | 1 | 20 | 1.3 | 98.7 |
| | 2 | 20 | 1.4 | 98.6 |
| | Average | 20 | 1.3 | 98.7 |
| S + M + L | 1 | 20 | 1.3 | 98.7 |
| | 2 | 10 | 0.7 | 99.3 |
| | Average | 15 | 1.0 | 99.0 |
| S + M + L + R | 1 | <10 Not detected | <0.7 | >99.3 |
| | 2 | <10 Not detected | <0.7 | >99.3 |
| | Average | <10 Not detected | <0.7 | >99.3 |
| S + M + L + R + H | 1 | <10 Not detected | <0.7 | >99.3 |
| | 2 | <10 Not detected | <0.7 | >99.3 |
| | Average | <10 Not detected | <0.7 | >99.3 |

F: Only the fan was operated (all lights were put out), S: the fan was operated and S was lighted up, M: M was lighted up, L: L was lighted up, R: R was lighted up, and H: H was lighted up.

TABLE 5

Deactivating effect on coxsackie virus
by an air disinfecting apparatus

| Germicidal lamp | Test | Number of survived viruses PFU/filter | Survival ratio % | Deactivated ratio of virus % |
|---|---|---|---|---|
| F (control) | 1 | 8.8 × 10² | 100 | 0 |
| | 2 | 7.6 × 10² | 100 | 0 |
| | Average | 8.2 × 10² | 100 | 0 |

TABLE 5-continued

Deactivating effect on coxsackie virus
by an air disinfecting apparatus

| Germicidal lamp | Test | Number of survived viruses PFU/filter | Survival ratio % | Deactivated ratio of virus % |
|---|---|---|---|---|
| S | 1 | $2.0 \times 10^2$ | 22.7 | 77.3 |
| | 2 | $1.2 \times 10^2$ | 15.8 | 84.2 |
| | Average | $1.6 \times 10^2$ | 19.5 | 80.5 |
| S + M | 1 | $1.6 \times 10^2$ | 18.2 | 81.8 |
| | 2 | $1.0 \times 10^2$ | 13.2 | 86.8 |
| | Average | $1.3 \times 10^2$ | 15.9 | 84.1 |
| S + M + L | 1 | 60 | 6.8 | 93.2 |
| | 2 | 40 | 5.3 | 94.7 |
| | Average | 50 | 6.1 | 93.9 |
| S + M + L + R | 1 | <20 Not detected | <2.3 | >97.7 |
| | 2 | <20 Not detected | <2.6 | >97.4 |
| | Average | <20 Not detected | <2.4 | >97.6 |
| S + M + L + R + H | 1 | <20 Not detected | <2.3 | >97.7 |
| | 2 | <20 Not detected | <2.6 | >97.4 |
| | Average | <20 Not detected | <2.4 | >97.6 |

F: Only the fan was operated (all lights were put out), S: the fan was operated and S was lighted up, M: M was lighted up, L: L was lighted up, R: R was lighted up, and H: H was lighted up.

As will be understood from Tables 1 to 5, *escherichia coli* of $1.2 \times 10^3$ CFU in average (in the case where only the fan was operated) became less than 10 CFU (not detected) in average by lighting up of two germicidal lamps S and M (Table 1). *Staphylococcus aureus* of $2.2 \times 10^3$ CFU in average (in the case where only the fan was operated) became less than 10 CFU (not detected) in average by lighting up of three germicidal lamps S, M, and L (Table 2). *Pseudomonas aeruginosa* of $1.2 \times 10^3$ CFU in average (in the case where only the fan was operated) became less than 10 CFU (not detected) in average by lighting up of two germicidal lamps S and M (Table 3). *Bacillus subtilus* spore of $1.5 \times 10^3$ CFU in average (in the case where only the fan was operated) became less than 10 CFU (not detected) in average by lighting up of three germicidal lamps S, M, and L, and lamp R (Table 4). *Coxsackie virus* of $8.2 \times 10^2$ PFU in average (in the case where only the fan was operated) became less than 20 (not detected) in average by lighting up of three germicidal lamps S, M, and L, and lamp R (Table 5).

The disinfected ratio of the *escherichia coli* was 98.7% in average when only germicidal lamp S was lighted up and higher than 99.2% in average when germicidal lamp M was further lighted up. The disinfected ratio of the *staphylococcus aureus* was 99.3% in average when two germicidal lamps S and M were lighted up and higher than 99.5% when germicidal lamp L was further lighted up. The disinfected ratio of the *pseudomonas aeruginosa* was 97.9% in average when only germicidal lamp S was lighted up and higher than 99.2% when germicidal lamp M was further lighted up.

The disinfected ratio of the *bacillus subtilus* spore was 99.0% in average when three germicidal lamps S, M, and L were lighted up and higher than 99.3% when lamp R was further lighted up. The deactivated ratio of *coxsackie virus* was 93.9% in average when three germicidal lamps S, M, and L were lighted up and higher than 97.6% when lamp R was further lighted up.

In the tests described above, the quantity of ozone generated in and discharged from the testing apparatus was large (the smell of ozone around the testing apparatus was sharp), and thus the limit of the time for atomizing bacteria or viruses, and recovering them in one test was 5 minutes at longest.

When a concentrated liquid containing $10^8$ CFU/ml of bacteria or a liquid containing $10^7$ PFU/ml of viruses was atomized in each of the tests, about $10^3$ of bacteria or about $10^2$ of viruses were detected at the exit side (air blowoff side) of the apparatus at the operation of the fan only (control), but the bacteria and viruses became "not detected" as described above when ultraviolet rays were radiated. Accordingly, the effect of disinfecting bacteria or deactivating viruses by the germicidal lamps in the testing apparatus is high, and the organisms adhered on the inside walls or the like of the apparatus are considered to be killed by the lighting up of germicidal lamps and an activating action by a catalyst.

With respect to the bacteria such as *escherichia coli*, *staphylococcus aureus*, and *pseudomonas aeruginosa*, disinfecting effect of higher than 99% in terms of disinfecting ratio can be expected by lighting up of three germicidal lamps S, M, and L. Whereas *bacillus subtilus* spore and *coxsackie virus* are high in resistance to ultraviolet rays and the activating action by the catalyst compared with the bacteria described above, disinfection of the bacterium at a disinfecting ratio of higher than 99% or the effect of deactivating the virus can be expected by lighting up of lamp R in addition to the germicidal lamps S, M, and L.

EXAMPLE 2

An experiment for purifying an air was conducted by employing a testing apparatus similar to that shown in FIG. 1 and using, as air to be used, an air containing 10 ppm of acetaldehyde as organic compound. On the inside walls of each of the device 10 for radiating ultraviolet rays of a medium wavelength and the device 13 for radiating ultraviolet rays of a long wavelength in the apparatus shown in FIG. 1, particles of titanium oxide of an orthorhombic crystal system (particles of brookite) were adhered as photocatalyst in the present invention. The result of the experiment is shown in Table 6. The result obtained when particles of a conventional anatase type titanium oxide were adhered on the walls is shown together as comparison in Table 6, and it can be understood from the Table that the content of acetaldehyde in the air was remarkably reduced in the case of the present invention.

TABLE 6

| | Photocatalyst | Residual ratio of acetaldehyde |
|---|---|---|
| Example | $TiO_2$ of orthorhombic crystal system (brookite) | 1% |
| Comparative Example | $TiO_2$ of tetragonal crystal system (anatase type) | 10% |

INDUSTRIAL APPLICABILITY

According to the present invention, purification treatments such as disinfection and deodorization of an air can efficiently be performed by radiating ultraviolet rays of predetermined wavelengths to the air in the presence of a photocatalyst; when particles of titanium oxide of an orthorhombic crystal system are used as catalyst in particular, it is possible to sever chains between carbon atoms (including, for example, double bonds, triple bonds, C—C bonds, and aromatic rings) in organic compounds contained in an air to oxidize and decompose the compounds down to low molecular weight compounds (carbonic acid gas and water); and thus purification treatments of exhaust gases containing hardly decomposable organic compounds becomes possible.

What is claimed is:

1. A method for purifying an oxygen containing gas comprising:
   a first step of generating ozone in the oxygen containing gas;
   a second step of radiating ultraviolet rays of a medium wavelength of 200 nm or longer, but shorter than 300 nm, to the gas treated in the first step to form active oxygen;
   a third step of radiating ultraviolet rays of a wavelength of 300 nm or longer, but shorter than 380 nm, to the gas treated in the second step to convert said active oxygen into an oxygen molecule in a ground state, at least one of said second step or said third step being conducted in the presence of a photocatalyst including at least one of particles of titanium oxide of an orthorhombic crystal system or particles of titanium oxide of an orthorhombic crystal system supporting fine particles of another metal; and
   a step of irradiating the oxygen containing gas treated in said third step, with rays radiated from an infrared lamp and with rays radiated from a halogen lamp to dry the gas.

2. The method according to claim 1 wherein said first step is a step of radiating ultraviolet rays of a short wavelength of shorter than 200 nm to the oxygen containing gas.

3. The method according to claim 2 wherein said particles of titanium oxide of an orthorhombic crystal system are particles of brookite.

4. The method according to claim 1 wherein said particles of titanium oxide of an orthorhombic crystal system are particles of brookite.

5. An apparatus for purifying an oxygen containing gas comprising:
   a first treating room having means of supplying the oxygen containing gas and a device for generating ozone in the supplied oxygen containing gas;
   a second treating room connected to the first treating room and having a device of radiating ultraviolet rays of a medium wavelength of 200 nm or longer, but shorter than 300 nm;
   a third treating room connected to the second treating room and having a device of radiating ultraviolet rays of along wavelength of 300 nm or longer, but shorter than 380 nm, said third treating room further having a drying room wherein a portion for irradiating the oxygen containing gas treated in the third treating room, with rays radiated from an infrared lamp and a portion for irradiating the oxygen containing gas treated in the third treating room, with rays radiated from a halogen lamp are installed in order; and
   means for discharging the oxygen containing gas treated in the third treating room outside the apparatus, at least a part of wall surfaces of at least one of said second treating room or said third treating room to which the ultraviolet rays are radiated being covered with a photocatalyst including at least one of particles of titanium oxide of an orthorhombic crystal system or particles of titanium oxide of an orthorhombic crystal system supporting particles of another metal.

6. The apparatus according to claim 5 wherein said device for generating ozone is a device for radiating ultraviolet rays of a wavelength of 100 nm or longer, but shorter than 200 nm.

7. The apparatus according to claim 5 wherein said particles of titanium oxide of an orthorhombic crystal system are particles of brookite.

* * * * *